United States Patent
Petrillo et al.

(10) Patent No.: US 6,555,677 B2
(45) Date of Patent: Apr. 29, 2003

(54) PHASE TRANSFER CATALYZED GLYCOSIDATION OF AN INDOLOCARBAZOLE

(75) Inventors: Daniel E. Petrillo, Hoboken, NJ (US); Steven A. Weissman, Short Hills, NJ (US); Shouichi Hiraga, Okazaki (JP); Nobuya Satake, Okazaki (JP); Kai Rossen, Hanau (DE)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/002,061

(22) Filed: Oct. 22, 2001

(65) Prior Publication Data

US 2002/0058803 A1 May 16, 2002

Related U.S. Application Data

(60) Provisional application No. 60/244,675, filed on Oct. 31, 2000.

(51) Int. Cl.[7] .............. C07H 19/00; C07H 19/22; C07H 17/02
(52) U.S. Cl. ............. 536/27.1; 536/27.11; 536/27.12; 536/17.7; 536/18.7; 536/29.1
(58) Field of Search .............. 536/27.1, 27.11, 536/27.12, 17.7, 18.7, 29.1

(56) References Cited

U.S. PATENT DOCUMENTS

| | | | |
|---|---|---|---|
| 4,808,613 A | | 2/1989 | Kaneko et al. |
| 4,977,254 A | * | 12/1990 | Homer et al. |
| 5,437,996 A | | 8/1995 | Kojiri et al. |
| 5,516,772 A | | 5/1996 | Glicksman et al. |
| 5,589,365 A | | 12/1996 | Kojiri et al. |
| 5,591,842 A | | 1/1997 | Kojiri et al. |
| 5,629,304 A | | 5/1997 | Murakata et al. |
| 5,668,271 A | | 9/1997 | Kojiri et al. |
| 5,804,564 A | | 9/1998 | Kojiri et al. |
| 5,922,860 A | * | 7/1999 | Kojiri et al. |
| 5,939,370 A | * | 8/1999 | Petit et al. |

FOREIGN PATENT DOCUMENTS

| EP | 0 545 195 B1 | 11/1995 |
|---|---|---|
| WO | WO 98/07433 | 2/1998 |

OTHER PUBLICATIONS

Starks, Charles M. et al, Phase Transfer Catalysis—Principles and Techniques, Academic Press, 1978 pp 1–10, 25–27, and 57–77.*
Exp. Opin. Ther. Pat. (2000) 10(5), pp. 635–666, by Long, et al.
Bioorg. Med. Chem. Lett. (2000), 10, pp. 419–422, by Ohkubo, et al.
Bioorg. Med. Chem. Lett. (1999), 9, pp. 145–150, by Zembower, et al.
Curr. Med. Chem. (2000), 7, pp. 1189–1212, by Prudhomm.
Bioorg. Med. Chem. Lett. (1999), 9, pp. 3307–3312, by Ohkubo, et al.
Tetrahedron (1996), vol. 52, No. 24, pp. 8099–8112, by Ohkubo, et al.
J. Org. Chem. (1982), 47, pp. 226–230, by Seela, et al.
J. Chem. Soc. Perkin Trans., 1, (1988), pp. 697–702, by Seela, et al.
J. Org. Chem, (1987), 52, pp. 5136–5143, by Seela, et al.
Synthesis (1990), 945–950, by Seela, et al.
Synthesis (1976), 124–125, by Barco, et al.
Synthesis (1976), 414–416, by Bocchi, et al.
J. Org. Chem. (1981), 46, pp.5413–5414, by Ghali, et al.
Tetrahedron (1999), 55, pp. 739–750, by Csuk, et al.
J. Org. Chem. (1999), 64, pp. 5670–5676, by Gilbert, et al.
J. Am. Chem. Soc. (1995), 117, pp. 4199–4200, by Stott, et al.
Carbohydrate Research (1980), 86, pp. 305–308, by Granata, et al.
Tetrahedron (1997), vol. 53, No. 2, pp. 585–592, by Ohkubo, et al.

* cited by examiner

*Primary Examiner*—James O. Wilson
*Assistant Examiner*—Traviss C. McIntosh
(74) *Attorney, Agent, or Firm*—Dianne Brown; Mark R. Daniel

(57) ABSTRACT

The present invention relates to a novel glycosidation process to make intermediates useful in the preparation of indolopyrrolocarbazole derivatives which inhibit the growth of tumor cells and are therefore useful in the treatment of cancer in mammals, and the like.

13 Claims, No Drawings

PHASE TRANSFER CATALYZED GLYCOSIDATION OF AN INDOLOCARBAZOLE

This application claims the benefit of Provisional Application No. 60/244,675, filed Oct. 31, 2000.

BACKGROUND OF THE INVENTION

The present invention relates to a novel glycosidation process to make intermediates useful in the preparation of indolopyrrolocarbazole derivatives which inhibit the growth of tumor cells and are therefore useful in the treatment of cancer in mammals, and the like.

In the field of cancer chemotherapy, a large number of compounds have already been put to practical use as antitumor agents. However, a need continues for the development of more efficacious compounds that work against a variety of tumors (see the Proceedings of the 47th General Meeting of the Japan Cancer Society, pp. 12–15 (1988)). This need has led to the development of indolocarbazole derivatives. (See U.S. Pat. Nos. 4,487,925; 4,552,842; 4,785,085; 5,591,842 and 5,922,860; Japanese Patent No. 20277/91; Journal of Antibiotics, Vol. 44, pp. 723–728 (1991); WO91/18003; WO 98/07433; and EP0545195 A1.) These compounds have been shown to act as topoisomerase inhibitors and therefore useful in the treatment of cancer (Cancer Chemother. Pharmacol. 34 (suppl): S41–S45 (1994)).

The success of these compounds in treating numerous cancers has necessitated the development of improved methods for their syntheses. (See Bioorg. & Med. Chem. Letters 2000, 10, 419; Tetrahedron 1997, 53, 5937; Tetrahedron 1997, 53, 585; and Synthesis 1976, 414.) The previously known methods, however, suffer from numerous problems, including the use of undesirable solvents, mercury or silver salts, low yields and formation of unwanted side-products necessitating tedious or protracted purification steps.

An object of this invention therefore is to provide a novel route to intermediates useful in the preparation of indolopyrrolocarbazole-derived antitumor substances while overcoming the problems inherent in the previously known syntheses.

SUMMARY OF THE INVENTION

The present invention is a novel glycosidation process to make intermediates useful in the preparation of indolopyrrolocarbazole derivatives which inhibit the growth of tumor cells and are therefore useful in the treatment of cancer in mammals, and the like, such as those of Formula I below.

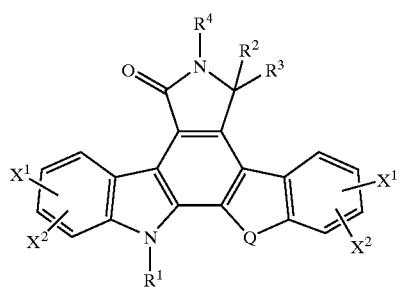

I

DETAILED DESCRIPTION OF THE INVENTION

An embodiment of the present invention is illustrated by a process for the preparation of a compound of Formula I,

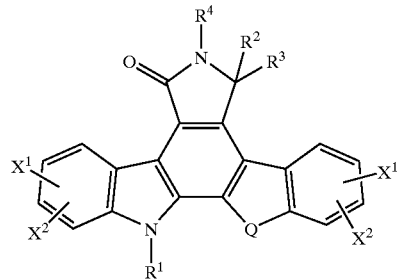

I wherein
Q is O, N—R, S, or $CH_2$;
$X^1$ and $X^2$ are independently selected from:
1) H,
2) halogen,
3) OH,
4) CN,
5) NC,
6) $CF_3$,
7) (C=O)$NO_2$,
8) (C=O)$C_1$–$C_6$ alkyl,
9) (C=O)O$C_1$–$C_6$ alkyl,
10) $OCH_2OCH_2CH_2Si(CH_3)_3$,
11) $NO_2$,
12) 9-fluorenylmethylcarbonyl,
13) $NR_5R_6$,
14) $OC_1$–$C_6$ alkyl,
15) $C_1$–$C_6$ alkyl,
16) $C_1$–$C_6$ alkylenearyl, and
17) $OC_1$–$C_6$ alkylenearyl;
R and $R^1$ are independently:
1) H,
2) (C=O)$C_1$–$C_6$ alkyl,
3) (C=O)$CF_3$,
4) (C=O)O$C_1$–$C_6$ alkyl,
5) 9-fluorenylmethylcarbonyl,
6) a furanose group, or
7) a pyranose group,
so long as one of R and $R^1$ is a furanose group or a pyranose group;
$R^2$ and $R^3$ are independently OH or H, or
$R^2$ and $R^3$ are taken together to form an oxo group;
$R^4$ is:
1) H,
2) $C_1$–$C_{10}$ alkyl,
3) CHO
4) (C=O)$C_1$–$C_{10}$ alkyl,
5) (C=O)O$C_1$–$C_{10}$ alkyl,
6) $C_0$–$C_{10}$ alkylenearyl, or
7) $C_0$–$C_{10}$ alkylene-$NR^5R^6$;
$R^5$ and $R^6$ are independently:
1) H,
2) ($C_1$–$C_8$ alkyl)—$(R^7)_2$,
3) (C=O)O($C_1$–$C_8$ alkyl),
4) 9-fluorenylmethylcarbonyl,
5) $OCH_2OCH_2CH_2Si(CH_3)_3$,
6) (C=O)($C_1$–$C_8$ alkyl),
7) (C⊚O)$CF_3$, or
8) ($C_2$–$C_8$ alkenyl)—$(R^7)_2$, or
$R^5$ and $R^6$ are taken together with the nitrogen to which they are attached to form N-phthalimido;

$R^7$ is:
1) H,
2) OH,
3) $OC_1$–$C_6$ alkyl, or
4) aryl, said aryl optionally substituted with up to two groups selected from OH, $O(C_1$–$C_6$ alkyl), and $(C_1$–$C_3$ alkylene)—OH;

which comprises the steps of:
(a) reacting a furanose or a pyranose with an activating reagent to produce an activated sugar; and
(b) coupling the activated sugar with a compound of Formula IV

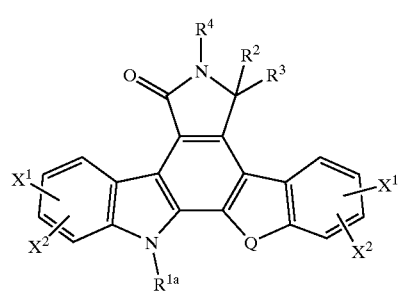

IV wherein $R^{1a}$ is H if Q is O, S, $CH_2$, or N—R and R is not H, otherwise $R^{1a}$ is selected from $R^1$; in the presence of an aqueous solution of alkali hydroxide and a phase transfer catalyst in a biphasic system to produce the compound of Formula I.

Another embodiment is the process described above, wherein

R and $R^1$ are independently selected from a furanose group of Formula IIA or a pyranose group of Formula IIB, when R or $R^1$ is defined as a furanose group or a pyranose group, respectively;

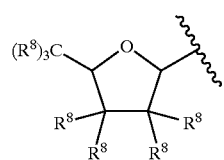

IIA

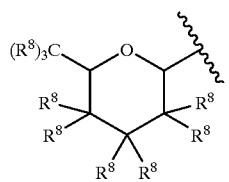

IIB $R^8$ is independently selected from:
1) hydrogen,
2) $C_1$–$C_6$ alkyl,
3) OH,
4) halogen,
5) $O(C_1$–$C_6$ alkyl),
6) $O(C_1$–$C_6$ alkylene)-aryl,
7) $OSO_2(C_1$–$C_6$ alkyl),
8) $OSO_2$aryl,
9) $OCH_2OCH_2CH_2Si(CH_3)_3$,
10) $O(C=O)(C_1$–$C_6$ alkyl),
11) $O(C=O)CF_3$,
12) azido, or
13) $NR^5R^6$, or two $R^8$'s on the same carbon are taken together to be oxo, =N—$R^5$, or =N=$R^7$; and the furanose or pyranose in Step (a) is a furanose of Formula IIIA or a pyranose of Formula IIIB, respectively;

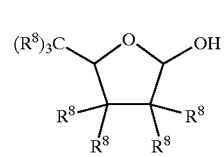

IIIA

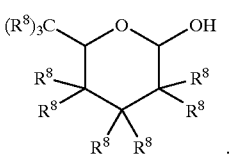

IIIB

In another embodiment, the activating reagent in Step (a) is selected from an acid halide, a sulfonate, a phosphate, a sulfate, a borate, or an acetate and the biphasic system in Step (b) is comprised of an organic solvent selected from a hydrocarbon, a nitrile, an ether, a halogenated hydrocarbon, a ketone, or an apolar aprotic solvent.

Yet another embodiment is the process described above wherein the activating reagent is selected from $SOCl_2$ or oxalyl chloride.

A further embodiment is the process described above wherein the biphasic system is comprised of methyl-t-butyl ether, dichloromethane, or trifluorotoluene.

In still another embodiment the phase transfer catalyst in Step (b) is $(R^a)_4M+A^-$;
$R^a$ is independently H or $C_1$–$C_{18}$ aliphatic hydrocarbon;
M is N or P; and
A is OH, F, Br, Cl, I, $HSO_4$, CN, $MeSO_3$, or $PhCH_2CO_2$.

A preferred embodiment is the process described above wherein the phase transfer catalyst is tricaprylmethyl ammonium chloride.

Another preferred embodiment is the process according to the description above, wherein the aqueous solution of alkali hydroxide in Step (b) has a concentration of about 5% to about 95% w/w and the alkali hydroxide is selected from lithium hydroxide, sodium hydroxide, potassium hydroxide, and cesium hydroxide.

Also favored is the process wherein the aqueous solution of alkali hydroxide has a concentration of about 45% to about 50% w/v and the alkali hydroxide is potassium hydroxide or sodium hydroxide.

A more preferred embodiment is a process for the preparation of a compound of Formula V,

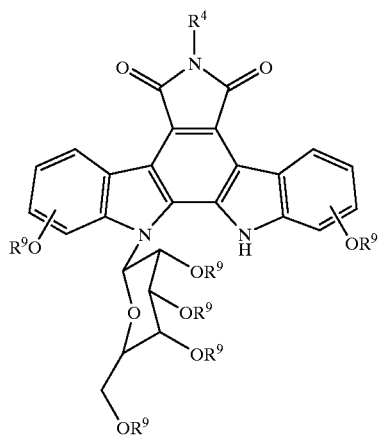

V

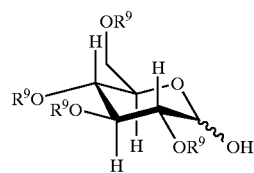

VI (b) coupling the activated sugar with a compound of Formula VII

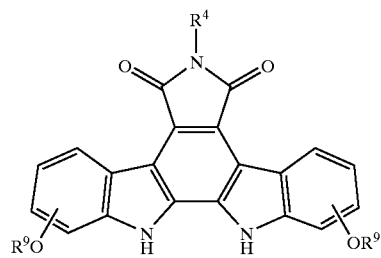

VII in the presence of an aqueous solution of an alkali hydroxide and tricaprylmethyl ammonium chloride in t-butyl methyl ether to produce the compound of Formula V.

And yet another preferred embodiment is a process for the preparation of a compound of Formula VIII,

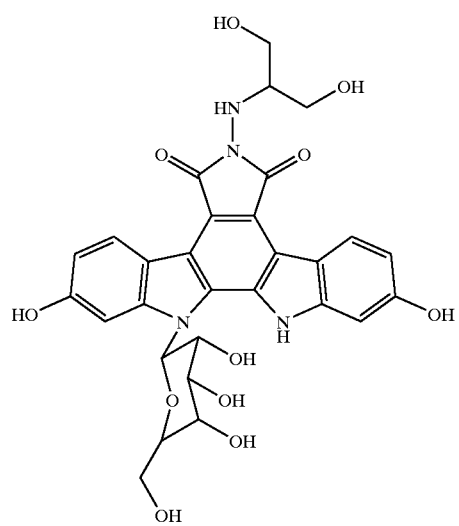

VIII wherein $R^4$ is:
1) H,
2) $C_1$–$C_{10}$ alkyl,
3) CHO
4) (C=O)$C_1$–$C_{10}$ alkyl,
5) (C=O)O$C_1$–$C_{10}$ alkyl,
6) $C_0$–$C_{10}$ alkylenearyl, or
7) $C_0$–$C_{10}$ alkylene-NR$^5$R$^6$;

$R^5$ and $R^6$ are independently:
1) H,
2) ($C_1$–$C_8$ alkyl)—(R$^7$)$_2$,
3) (C=O)O($C_1$–$C_8$ alkyl),
4) 9-fluorenylmethylcarbonyl,
5) OCH$_2$OCH$_2$CH$_2$Si(CH$_3$)$_3$,
6) (C=O)($C_1$–$C_8$ alkyl),
7) (C=O)CF$_3$, or
8) ($C_2$–$C_8$ alkenyl)—(R$^7$)2, or $R^5$ and $R^6$ are taken together with the nitrogen to which they are attached to form N-phthalimido;

$R^7$ is:
1) H,
2) OH,
3) O$C_1$–$C_6$ alkyl, or
4) aryl, said aryl optionally substituted with up to two groups selected from OH, O($C_1$–$C_6$ alkyl), and ($C_1$–$C_3$ alkylene)—OH;

$R^9$ is:
1) H,
2) $C_1$–$C_6$ alkyl,
3) ($C_1$–$C_6$ alkylene)-aryl,
4) SO$_2$($C_1$–$C_6$ alkyl),
5) SO$_2$aryl,
6) CH$_2$OCH$_2$CH$_2$Si(CH$_3$)$_3$,
7) (C=O)($C_1$–$C_6$ alkyl), or
8) (C=O)CF$_3$;

which comprises the steps of:
(a) reacting a sugar derivative of Formula VI with an acid chloride to produce the activated sugar; and which comprises the steps of:
(a) reacting a sugar derivative of Formula IX with thionyl chloride to produce the activated sugar;

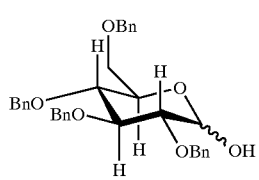

IX (b) coupling the activated sugar with a compound of Formula X

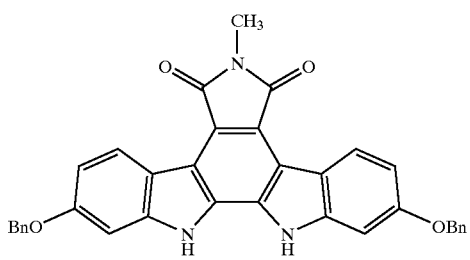

in the presence of an aqueous solution of potassium hydroxide or sodium hydroxide and tricaprylmethyl ammonium chloride in t-butyl methyl ether to form the glycosidated compound XI;

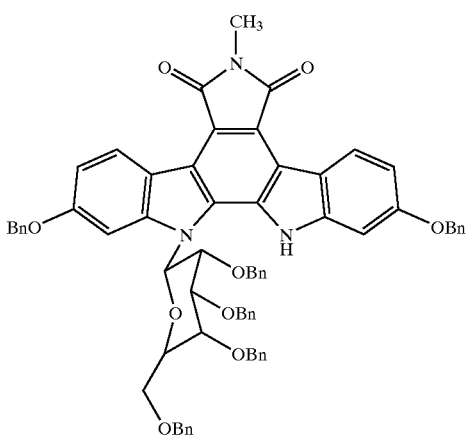

(c) deprotecting the glycosidated product XI by reacting it with catalytic palladium in he presence of hydrogen gas to form the deprotected glycosidated product XII;

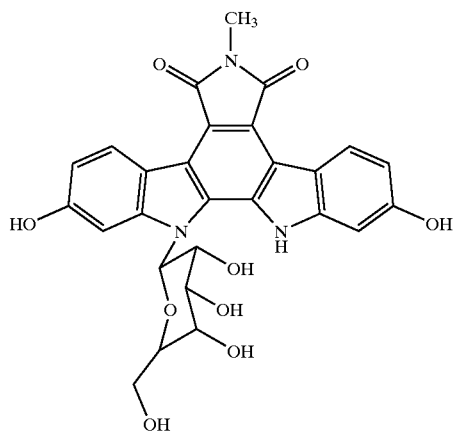

(d) reacting the deprotected glycosidated product XII with an aqueous solution of alkali hydroxide to form anhydride XIII; and

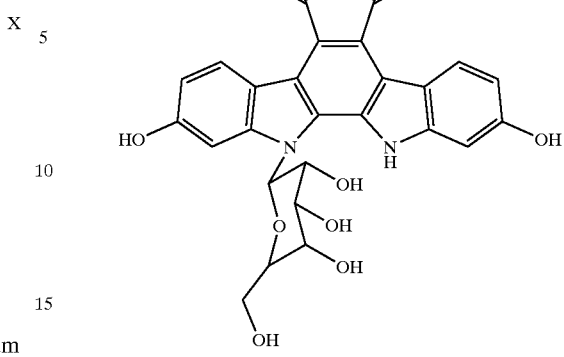

(e) reacting anhydride XIII with 2-hydrazino-1,3-propanediol to produce the compound of Formula VIII.

Also preferred is the process as described above to make a compound of Formula V wherein Step (A) is conducted in t-butyl methyl ether or tetrahydrofuran at a temperature of about −10° C. to about 30° C. and Step (B) is conducted at a temperature of about 0° C. to about 40° C.

And a final embodiment is the process described above, wherein the potassium hydroxide or sodium hydroxide in step (b) is added before the tricaprylmethyl ammonium chloride.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. $X^1$, $X^2$, $R^8$, $R^9$ etc.) occurs more than one by time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

As used herein, "alkyl" is intended to include both branched, straight-chain, and cyclic saturated aliphatic hydrocarbon groups having the specified number of carbon atoms. For example, $C_1$–$C_6$, as in "$C_1$–$C_6$ alkyl" is defined to include groups having 1, 2, 3, 4, 5, or 6 carbons in a linear, branched, or cyclic arrangement. For example, "$C_1$–$C_6$ alkyl" specifically includes methyl, ethyl, propyl, butyl, pentyl, hexyl, and so on, as well as cycloalkyls such as cyclopropyl, methylcyclopropyl, dimethylcyclobutyl, cyclobutyl, cyclopentyl, and cyclohexyl, and so on. The alkyl substituents may be unsubstituted or substituted with one to three substituents selected from halogen, $C_1$–$C_6$ alkyl, OH, $OC_1$–$C_6$ alkyl, $O(C=O)C_1$–$C_6$ alkyl, $O(C=O)OC_1$–$C_6$ alkyl, amino, amido, $CO_2H$, CN, $NO_2$, $N_3$, $C_1$–$C_6$ perflouroalkyl, and $OC_1$–$C_6$ perflouroalkyl. "Alkoxy" represents an alkyl group of indicated number of carbon atoms attached through an oxygen bridge.

The term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

In certain instances, substituents may be defined with a range of carbons that includes zero, such as ($C_0$–$C_6$) alkylene-$NR^5R^6$. If $R^5$ and $R^6$ are taken as H in this case, this definition would include $NH_2$, as well as —$CH_2NH_2$, —$CH_2CH_2NH_2$, $CH(CH_3)CH_2CH(CH_3)NH_2$, —$CH_2CH(NH_2)CH_3$, and so on. It is intended in these cases that the substituent on the bivalent radical can be attached at any point and not limited to the terminal position.

As used herein, "aryl" is intended to mean substituted and unsubstituted phenyl or naphthyl. If substituted, it may be substituted with one to three substituents selected from halogen, $C_1$–$C_6$ alkyl, OH, $OC_1$–$C_6$ alkyl, $O(C=O)C_1$–$C_6$ alkyl, $O(C=O)OC_1$–$C_6$ alkyl, amino, amido, $CO_2H$, CN, $NO_2$, $N_3$, $C_1$–$C_6$ perflouroalkyl, and $OC_1$–$C_6$ perflouroalkyl.

As appreciated by those of skill in the art, "halo" or "halogen" as used herein is intended to include chloro, fluoro, bromo and iodo.

When definitions such as "($C_1$–$C_8$ alkyl)—($R^7$)$_2$" are used, it is intended that the variable $R^7$ be attached at any point along the alkyl moiety. Therefore, if $R^7$ is defined as OH in this case, the definition would include the following: $CH_2OH$, $CH_2CH_2OH$, $CH(CH_3)CH(OH)CH_3$, $CH(CH_3)CH(OH)CH_2$—$CH(OH)CH_3$, and so on.

The term "alkylene" and "alkenylene" simply refer to an alkyl or alkenyl group as defined above, respectively, of the specified number of carbons that is divalent. For example, "$C_1$–$C_4$ alkylene" includes —$CH_2$—, —$CH_2CH_2$—, —$CH(CH_3)CH_2$—, and so on.

The definitions of R and $R^1$ include furanose and pyranose sugar derivatives. Preferred sugar derivatives are O-protected pyranoses, such as D-glucopyranose; 6-deoxy-6,6-difluoro-D-glucopyranose; 6-deoxy-6-azido-D-glucopyranose; 6-amino-6-deoxy-D-glucopyranose; 6-azido-D-glucopyranose; 6-amino-D-glucopyranose; 4-deoxy-4,4-difluoro-6-deoxy-6-azido-D-glucopyranose; 2-fluoro-D-glucopyranose; D-galactopyranose; 4-deoxy-D-galactopyranose; 4-deoxy-D-glucopyranose; and 4-methoxy-D-glucopyranose. (see, for examples, WO 98/07433, hereby incorporated by reference). Preferred furanoses include xylofuranose, arabinofuranose, ribofuranose, allofuranose, and 2-deoxyribofuranoses.

$R^9$ can generally be any known O-protecting group. Examples of such protecting groups include, but are not limited to: benzyl, p-nitrobenzyl, tolyl, and the like. A more preferred protecting group is benzyl (Bn), i.e., $CH_2Ph$. Other suitable protecting groups will be known to those of skill in the art, examples of which can be found in *Protective Groups in Organic Synthesis* by Peter G. M. Wuts and Theodora W. Greene; John Wiley & Sons, 3$^{rd}$ ed. (1999).

As used herein, "biphasic system" refers to a two-phase solvent system consisting of an aqueous phase and an organic phase.

The choice of activating reagent to activate the sugar for coupling can be readily discerned by those skilled in the art. Examples of such reagents include acid halides (such as $SOCl_2$, $POCl_3$, $SOBr_2$, $POBr_3$, $PBr_3$ and oxalyl chloride), sulfonyl halides, and so on. The preferred reagents are thionyl chloride and oxalyl chloride. The most preferred is thionyl chloride. Other useful reagents in the activation include triphenyl phosphine/$I_2$, and triphenyl phosphine/azidodicarboxylate.

The appropriate solvent to be used in the reaction to activate the sugar can be ascertained by the ordinary chemist. Preferred solvents are hydrocarbons (such as toluene, xylenes, heptane, and hexane), nitriles (such as acetonitrile), ethers (such as t-butyl methyl ether and tetrahydrofuran), halogenated hydrocarbons (such as methylene chloride, carbontetrachloride, chloroform, trifluorotoluene and dichlorobenzene) ketones (such as methyl isobutyl ketone and acetone), and apolar aprotic solvents (such as N,N-dimethylformamide and 1-methyl-2-pyrrolidinone). More preferred solvents are t-butyl methyl ether and tetrahydrofuran. The most preferred solvent is t-butyl methyl ether.

The activation reaction can be performed at temperatures ranging from about −50° C. to about 200° C. The preferred temperatures are about −10° C. to about 30° C.

Similarly, the appropriate solvent to use in the biphasic coupling reaction will be readily discernible to the skilled artisan. Appropriate solvents include hydrocarbons (such as toluene, xylenes, heptane, and hexane), nitriles (such as acetonitrile), ethers (such as t-butyl methyl ether and tetrahydrofuran), halogenated hydrocarbons (such as methylene chloride, carbontetrachloride, chloroform, trifluorotoluene and dichlorobenzene) ketones (such as methyl isobutyl ketone and acetone), and apolar aprotic solvents (such as N,N-dimethylformamide and 1-methyl-2-pyrrolidinone). The preferred solvents are t-butyl methyl ether, dichloromethane, and trifluorotoluene.

The coupling reaction can be performed at temperatures ranging from about −50° C. to about 200° C. The preferred temperatures are about 0° C. to about 40° C.

The preferred bases for the coupling reaction are alkali hydroxides, such as lithium, sodium, potassium, and cesium hydroxide. Potassium hydroxide and sodium hydroxide are more preferred. The base concentration in water can vary from about 5% w/w to about 95% w/w. The more preferred concentrations are about 45% to about 50% w/w.

The preferred phase transfer reagents in the coupling reaction are of the general formula $(R^a)_4M+A^-$, wherein $R^a$ is independently H or $C_1$–$C_{18}$ aliphatic hydrocarbon; M is N or P; and A is OH, F, Br, Cl, I, $HSO_4$, CN, $MeSO_3$, or $PhCH_2CO_2$. A preferred phase transfer catalyst is tricaprylmethyl ammonium chloride. Other suitable phase transfer catalysts include, but are not limited to, tris-[2-(2-methoxyethoxy)ethyl]amine (TDA-1); $BnEt_3N+Cl$—; and $(Bu)_3NH+HSO_4$—.

Synopsis of Schemes

Scheme A illustrates one possible generalized approach to the preparation of the glycosidation substrate A-6. Other approaches are known in the art, some of which are taught by Kojiri et al. in U.S. Pat. No. 5,922,860 (issued Jul. 13, 2000) and hereby incorporated by reference. Scheme B shows the phase transfer catalyzed glycosidation of A-6 to produce intermediates of type B-3. Schemes C and D show possible further modifications to afford compounds known to be useful as topoisomerase inhibitors.
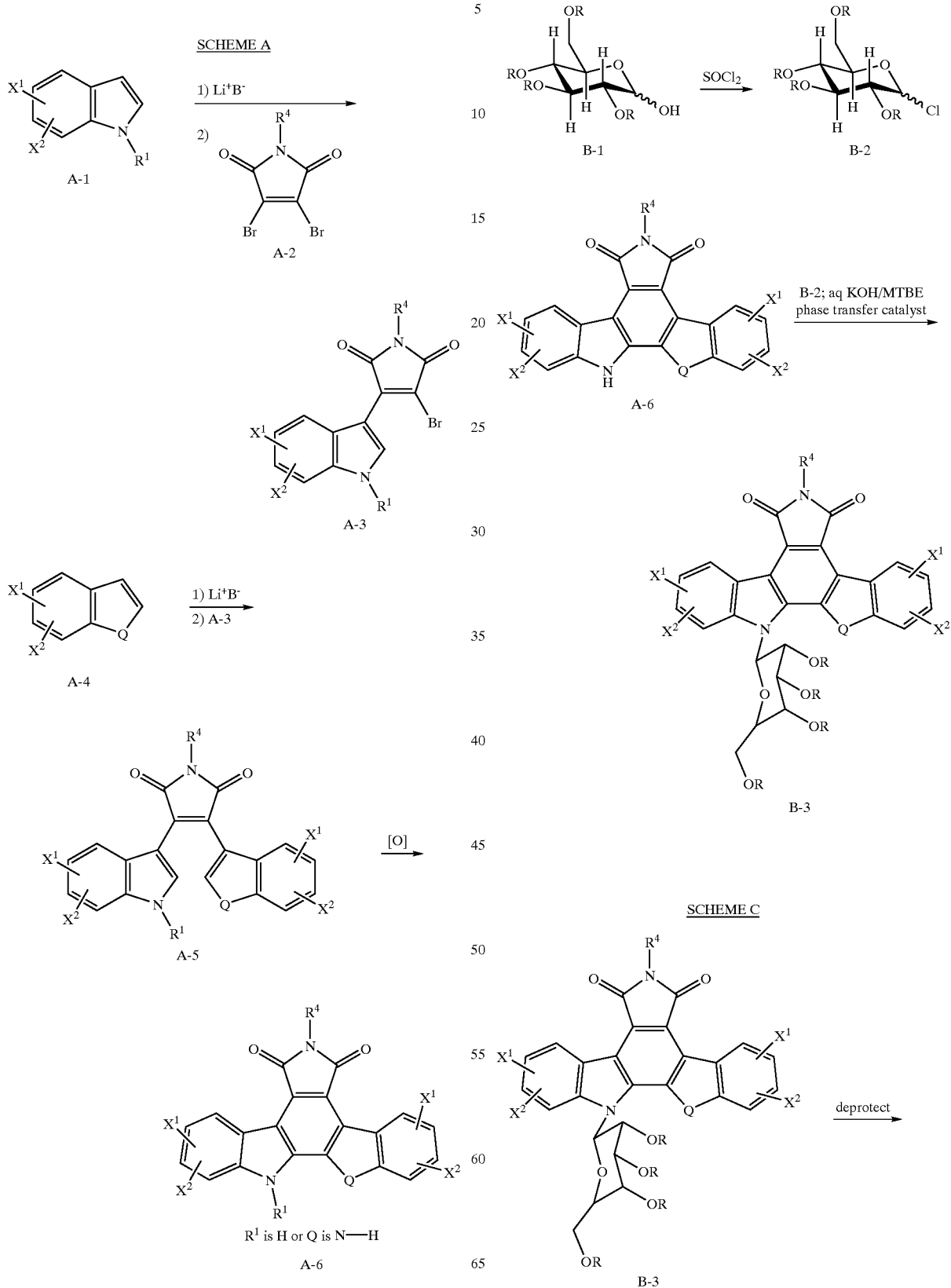

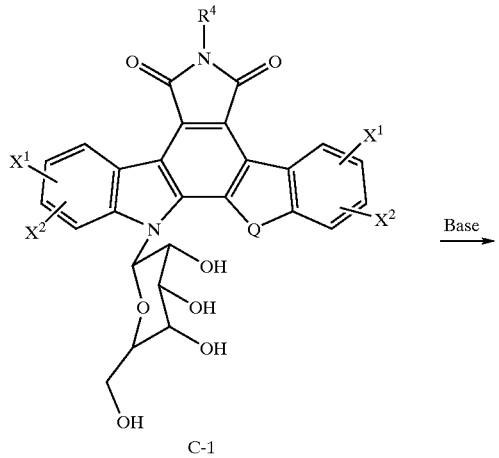

C-1

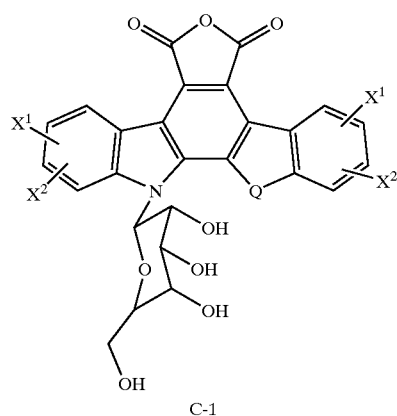

C-1

SCHEME D

C-1

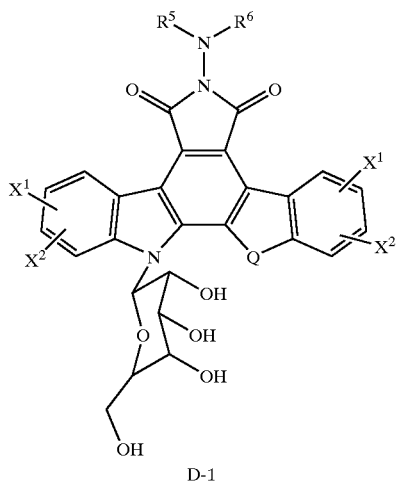

D-1

EXAMPLES

Examples provided are intended to assist in a further understanding of the invention. Particular materials employed, species and conditions are intended to be further illustrative of the invention and not limiting of the reasonable scope thereof.

Intermediate 5, used in the glycosidation reaction of this invention, can be obtained by the method disclosed by Kojiri et al. in U.S. Pat. No. 5,922,860 (issued Jul. 13, 2000) and hereby incorporated by reference. The procedure is outlined below in Examples 1 through 5.

Example 1

Preparation of the Compound Represented by Formula 1

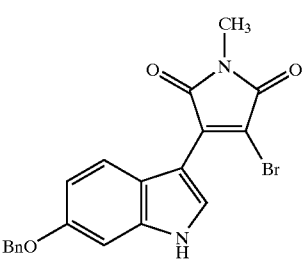

284 g of 6-benzyloxyindole was dissolved in 3 liters of THF, and 2.7 liters of lithium hexamethyldisilazide (as a 1M solution in THF) was added thereto. After this mixture was stirred under an atmosphere of nitrogen at −10° C. for 45 minutes, 3 liters of a THF solution containing 340 g of 2,3-dibromo-N-methylmaleimide was added dropwise thereto over a period of 1 hour. After completion of the addition, the resulting mixture was stirred at 0° C. for 15 minutes. The reaction mixture was poured into 10 liters of 2N hydrochloric acid and extracted with 30 liters of ethyl acetate. The organic layer was washed with a saturated aqueous solution of sodium hydrogen carbonate and then a saturated aqueous solution of sodium chloride, dried and concentrated. The resulting residue was recrystallized from methanol to obtain desired compound 1. HRMS (m/z): found 410.0292, calcd 410.0266 [as $C_{20}H_{15}N_2O_3Br$] IR (KBr, cm$^{-1}$): 3330, 3318, 1762, 1701, 1606, 1511, 1450, 1165, 1135, 1041, 794. $^1$H-NMR (300 MHz, CDCl$_3$, δ ppm): 8.60 (1H, brs), 7.96 (1H, d, J=8.1 Hz), 7.94 (1H, d, J=2.5 Hz), 7.33–7.47 (5H, m), 7.00 (1H, dd, J=2.5, 8.8 Hz), 6.97 (1H, d, J=2.5 Hz), 5.13 (2H, s), 3.16 (3H, s).

Example 2

Preparation of the Compound Represented by Formula 2

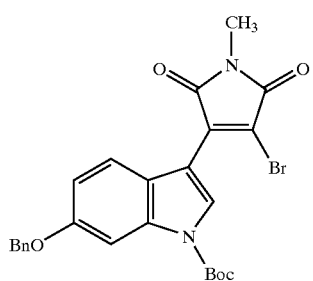

2

1.00 g of compound 1 obtained in Example 1, 637 mg of di-tert-butyl dicarbonate and 3 mg of 4-N,N-dimethylaminopyridine were dissolved in 200 mL of THF, and this solution was stirred at room temperature for 1 hour. After the reaction mixture was concentrated, the resulting residue was recrystallized from ethyl acetate-hexane to obtain the desired compound (2). IR (KBr, cm$^{-1}$): 1740, 1714, 1614, 1527, 1487, 1443, 1373, 1227, 1153. HRMS (m/z): found 510.0771, calcd 510.0791 [as $C_{25}H_{23}N_2O_5Br$] $^1$H-NMR (300 MHz, CDCl$_3$, δ. ppm): 8.10 (1H, s), 7.91 (1H, d, J=2.3 Hz), 7.73 (1H, d, J=8.9 Hz), 7.34–7.50 (5H, m), 7.03 (1H, dd, J=2.3, 8.5 Hz), 5.16 (2H, s), 3.18 (3H, s), 1.68 (9H, s).

Example 3

Preparation of the Compound Represented by Formula 3

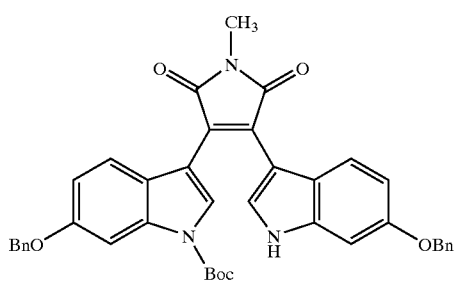

3

218.4 mg of 6-benzyloxyindole was dissolved in 20 mL of THF, and 2.35 mL of lithium hexamethyldisilazide (as a 1M solution in THF) was added thereto. After this mixture was stirred under an atmosphere of nitrogen at 0° C. for 15 minutes, 10 mL of a THF solution containing 500 mg of the compound (2) obtained in Example 2 was added dropwise thereto over a period of 10 minutes. After completion of the addition, the resulting mixture was stirred at room temperature for 0.5 hour. The reaction mixture was poured into 100 mL of 2N hydrochloric acid and extracted with 400 mL of ethyl acetate. The organic layer was washed with water, a saturated aqueous solution of sodium hydrogen carbonate and then a saturated aqueous solution of sodium chloride, dried and concentrated. The resulting residue was recrystallized from toluene-hexane to obtain the desired compound (3). HRMS (m/z): found 653.2556, calcd 653.2526 [as $C_{40}H_{35}N_3O_6$] IR (KBr, cm$^{-1}$): 1740, 1701, 1646, 1623, 1543, 1445, 1155. $^1$H-NMR (300 MHz, CDCl$_3$, δ ppm): 8.41 (1H, brs), 7.97 (1H, s), 7.84 (1H, brs), 7.68 (1H, brs), 7.16–7.43 (10H, m), 6.98 (1H, d, J=9.2 Hz), 6.85 (1H, brs), 6.74 (1H, d, J=9.2 Hz), 6.58 (1H, d, J=9.2 Hz), 6.52 (1H, d, J=9.2 Hz), 5.05 (2H, s), 5.02 (2H, s), 3.19 (3H, s), 1.67 (9H, s).

Example 4

Preparation of the compound represented by formula 4

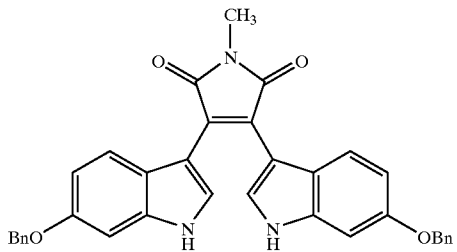

4

100 mg of the compound (3) obtained in Example 3 was dissolved in 10 mL of methylamine (as a 40% solution in methanol), and this solution was stirred at room temperature for 30 minutes. After the reaction mixture was concentrated, the resulting residue was recrystallized from dichloromethane-acetone-hexane to obtain 68.6 m of the desired compound (4). HRMS (m/z): found 553.1982, calcd 553.2002 [as $C_{35}H_{27}N_3O_4$] IR (KBr, cm$^{-1}$): 3419, 3350, 1759, 1697, 1620, 1533, 1454, 1383, 1292, 1167. $^1$H-NMR (300 MHz, DMSO-d$_6$, δ ppm): 11.48 (2H, s), 7.62 (2H,s), 7.28–7.45 (10H, m), 6.95 (2H, d, J=1.2 Hz), 6.70 (2H, d, J=8.7 Hz), 6.39 (2H, dd, J=1.2, 8.7 Hz), 5.04 (4H, s), 3.03(3H, s).

Example 5

Preparation of the Compound Represented by Formula 5

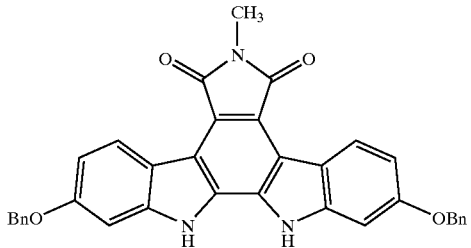

5

1.01 g of the compound (4) obtained in Example 4 and 456.1 mg of 2,3-dichloro-5,6-dicyano-1,4-benzoquinone were dissolved in 50 mL of toluene, and this solution was stirred at 110° C. for 40 minutes. After the reaction mixture was returned to room temperature, the insoluble matter was filtered off and washed with 30 mL of methanol. The residue was recrystallized from dimethyl sulfoxidedichloromethane-methanol to obtain the desired compound (5). HRMS (m/z): found 551.1829, calcd 551.1845 [as $C_{35}H_{25}N_3O_4$] IR (KBr, cm.$^{-1}$): 3257, 1740, 1675, 1620, 1571, 1402,1246,1178. $^1$H-NMR (300 MHz, DMSO-d$_6$, δ ppm): 11.46 (2H, s), 8.79 (2H, d, J=8.5 Hz), 7.53 (4H, d, 8.5 Hz), 7.35–7.44 (8H, m), 7.02 (2H, 0.8 Hz), 5.25 (4H, s), 3.13 (3H, s).

Example 6

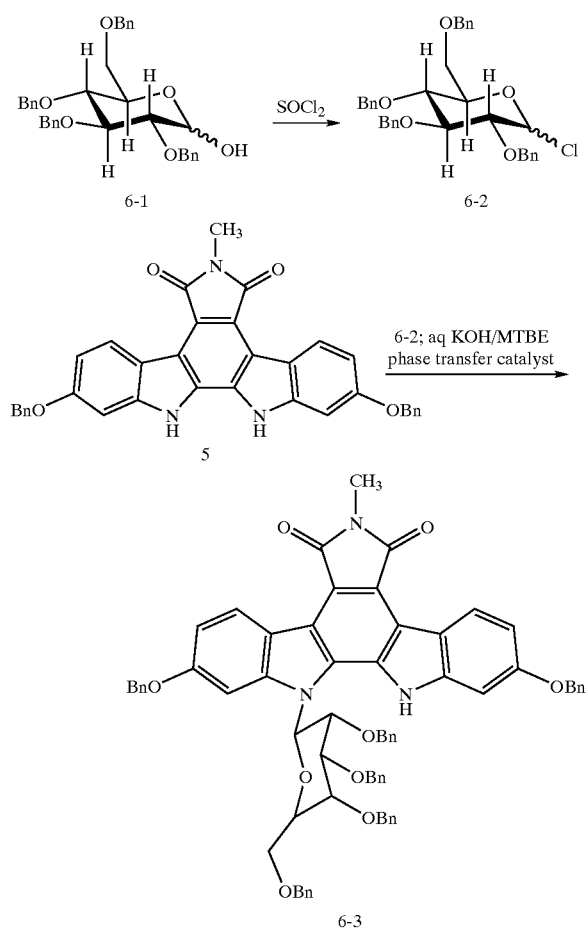

Step 1:

100 g (185 mmols) of 2,3,4,6-O-tetrabenzyl-D-glucopyranose (6-1) was combined with 360 mL of DMF at 23° C. and then cooled to 9° C. Thionyl chloride (16.2 mL; 222 mols) was added slowly over 15 minutes, during which time the temperature rose to 20° C. The solution was warmed to about 30° C. and aged for 1 hour. The solution was then cooled to −10° C. and 10% KOH w/w (about 150 mL) was added, during which time the temperature did not exceed 0° C. The solution was warmed to 22° C. The aqueous layer was extracted with t-butyl methyl ether (MTBE) (1×300 mL). The combined organic layers were then washed with brine (1×150 mL) and water (1×200 mL). The solution was concentrated under reduced pressure to the 350 mL level and used in the next step without further purification.

Step 2:

72 g (131 mmol) of compound 5 from Example 5 above were dissolved in 600 mL of MTBE and stirred for 10 minutes at 23° C. The solution of 6-2 made in Step 1 above was then added and, after 10 minutes, 45% w/w aqueous KOH (300 mL) was added. After an additional 10 minutes, 40% w/w Aliquat® 336 (72 g in 110 g MTBE) was added slowly over 22 minutes. Aliquat® 336 is a brand name of tricaprylmethylammonium chloride sold by Aldrich Chemical Co., Inc., in Milwaukee, Wis. The solution was aged at 23° C. for 6 hours and 350 mL of water were then added and allowed to mix for 5 minutes. The layers were separated and the aquoeus layer was washed with MTBE (1×300 mL). The combined organic layers were then washed with 10% w/w citric acid (1×300 mL) and water (1×300 mL). The organic layer was stirred at 22° C. overnight during which time the product (6-3) began to crystallize. The solution was then concentrated at atmospheric pressure (bp 55° C.) to the 625 mL level. At this point, the solution was cooled to 23° C. and methanol (225 mL) was added slowly over 1 hour. The slurry was then cooled to −5° C. and aged for 45 minutes. The solids were isolated and washed with chilled 1:1 methanol/MTBE (2×400 mL). Drying in vacuo at 25°–40° C. provided the product 6-3 with over 99% purity by liquid chromatography.

The following examples, taken from Kojiri et al. in U.S. Pat. No. 5,922,860 and previously incorporated by reference, illustrate the use of the glycosidation products in the synthesis of a known topoisomerase inhibitor (9).

Example 7

Preparation of the Compound Represented by Formula 7

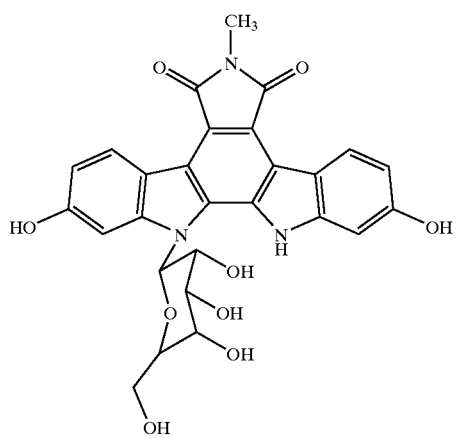

100 mg of compound 6-3 was dissolved in 6 mL of chloroform-methanol (2:1), and a catalytic amount of palladium black was added thereto. This mixture was stirred under an atmosphere of hydrogen for 2 hours. After the catalyst was filtered off, the filtrate was concentrated. The resulting residue was crystallized from methanol-acetone-ethyl acetate-hexane, developed with Sephadex LH-20, eluted with chloroform-methanol-ethanol-tetrahydrofuran (5:2:2:1), and recrystallized from acetone-methanol-hexane to obtain the desired compound (7). HRMS (m/z): found 533.1429, calcd 533.1434 [as $C_{27}H_{23}N_3O_9$] IR (KBr, cm$^{-1}$): 3328, 1733, 1683, 1678, 1540, 1417, 1126, 1081, 611. $^1$H-NMR (300 MHz, DMSO-d6δ ppm): 11.20 (1H, s), 9.76(1H, s), 9.74 (1H, s), 8.88 (1H, d, J=8.6 Hz), 8.80 (1H, d, J=8.6 Hz), 7.18 (1H, d, J=2.1 Hz), 6.99 (1H, d, J=2.1 Hz), 6.82 (1H, dd, J=2.1, 8.6 Hz), 6.80 (1H, dd, J=2.1, 8.6 Hz), 5.97 (1H, J=8.9 Hz), 5.86 (1H, t, J=4.0 Hz), 5.33 (1H, d, J=4.9 Hz), 5.12 (1H, d, J=4.3 Hz), 4.94 (1H, d, J=5.2 Hz), 4.02 (1H, dd, J=3.0, 10.7 Hz), 3.94 (1H, m), 3.78(1H, m), 3.52 (2H, m), 3.16(3H, s).

Example 8

Preparation of the Compound Represented by Formula 8

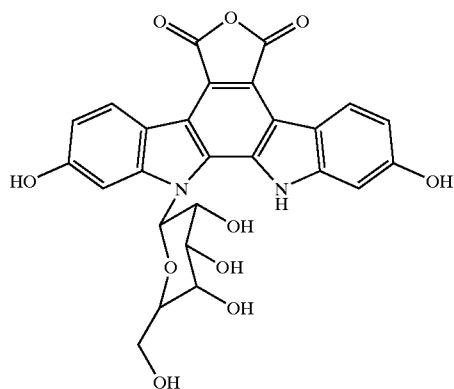

1.2 g the compound (7) was dissolved in 40 mL of a 10% aqueous solution of potassium hydroxide, and this solution was stirred at room temperature for 1 hour. The reaction mixture was neutralized by the addition of 40 mL of 2N hydrochloric acid, and then extracted with 1 liter of methyl ethyl ketone. The organic layer was washed with a saturated aqueous solution of sodium chloride, dried and concentrated. The resulting residue was recrystallized from acetone-heptane to obtain the desired compound (8). HRMS (m/z): found 520.1147, calcd 520.1118 [as $C_{26}H_{20}N_2O_{10}$] IR (KBr, cm$^{-1}$): 3311, 1810, 1739, 1652, 1626, 1558, 1405, 1091, 611. $^1$H-NMR (300 MHz, DMSO-d$_6$, δ ppm): 11.4 (1H, s), 9.95 (1H, s), 9.92 (1H, s), 8.69 (1H, d, J=7.7 Hz), 8.63 (1H, d, J=7.7 Hz), 7.25 (1H, d, J=1.5 Hz), 7.03 (1H, d, J=1.5 Hz), 6.90 (1H, dd, J=1.5, 7.7 Hz), 6.87 (1H, d, J=1.5, 7.7 Hz), 6.06 (1H, d, J=8.0 Hz), 5.95 (1H, t, J=4.6 Hz), 5.38 (1H, d, J=5.1 Hz), 5.16 (1H, d, J=5.2 Hz), 4.99 (1H, d, J=5.2 Hz), 3.30–4.10 (6H, m).

Example 9

Preparation of the Topoisomerase Inhibitor Represented by Formula 9

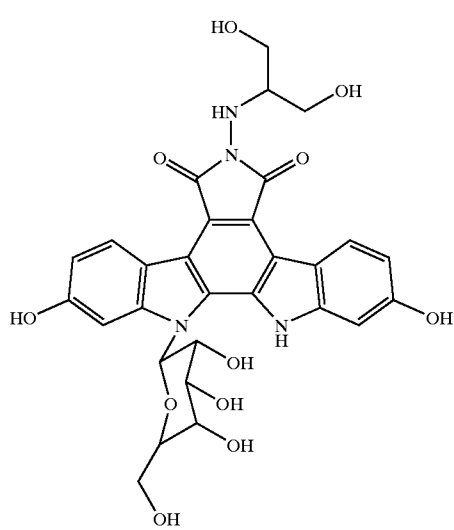

500 mg of compound 8 was dissolved in 50 mL of DMF, and 152 mg of 2-hydrazino-1,3-propanediol was added thereto. This mixture was stirred at 80° C. for 1 hour. After the reaction mixture was concentrated, the resulting residue was purified with Sephadex LH-20 (chloroform-methanol-ethanol-water=5:2:2:1) to obtain compound 9. HRMS (m/z): found 609.1816, calcd 609.1833 [as $C_{29}H_{28}N_4O_{11}$] IR (KBr, cm.sup.$^{-1}$): 3415, 3353, 1749, 1652, 1575, 1540, 1375, 1197,609. $^1$H-NMR (300 MHz, DMSO-d$_6$, δ ppm): 11.20 (1H, s), 9.78 (1H, s), 9.75 (1H, s), 8.87 (1H, d, J=8.6 Hz), 8.79 (1H, d, J=8.6 Hz), 7.18 (1H, d, J=2.0 Hz), 6.98 (1H, d, J=2.0 Hz), 6.82 (1H, dd, J=2.0, 8.6 Hz), 6.80 (1H, dd, J=2.0, 8.6 Hz), 5.97 (1H, J=8.3 Hz), 5.86 (1H, d, J=3.8 Hz), 5.55 (1H, d, J=2.6 Hz), 5.32 (1H, d, J=4.6 Hz), 5.11 (1H, d, J=5.3 Hz), 4.91 (1H, d, J=5.1 Hz), 4.53 (2H, t, J=5.4 Hz), 4.02 (1H, m), 3.85–3.95 (2H, m), 3.78 (1H, m), 3.40–3.60 (6H, m), 3.20–3.30 (1H, m).

What is claimed is:

1. A process for the preparation of a compound of Formula I,

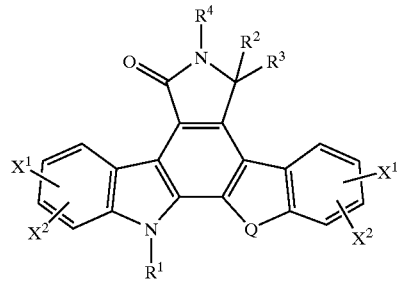

wherein

Q is O, N—R, S, or CH$_2$;

X$^1$ and X$^2$ are independently selected from:
1) H,
2) halogen,
3) OH,
4) CN,
5) NC,
6) CF$_3$,
7) (C=O)NO$_2$,
8) (C=O)C$_1$–C$_6$ alkyl,
9) (C=O)OC$_1$–C$_6$ alkyl,
10) OCH$_2$OCH$_2$CH$_2$Si(CH$_3$)$_3$,
11) NO$_2$,
12) 9-fluorenylmethylcarbonyl,
13) NR$_5$R$_6$,
14) OC$_1$–C$_6$ alkyl,
15) C$_1$–C$_6$ alkyl,
16) C$_1$–C$_6$ alkylenearyl, and
17) OC$_1$–C$_6$ alkylenearyl;

R and R$^1$ are independently:
1) H,
2) (C=O)C$_1$–C$_6$ alkyl,
3) (C=O)CF$_3$,
4) (C=O)OC$_1$–C$_6$ alkyl,
5) 9-fluorenylmethylcarbonyl,
6) a furanose group, or
7) a pyranose group, so long as one of R and $R^1$ is a furanose group or a pyranose group;

$R^2$ and $R^3$ are independently OH or H, or $R^2$ and $R^3$ are taken together to form an oxo group;

$R^4$ is:
1) H,
2) $C_1$–$C_{10}$ alkyl,
3) CHO,
4) (C=O)$C_1$–$C_{10}$ alkyl,
5) (C=O)O$C_1$–$C_{10}$ alkyl,
6) $C_0$–$C_{10}$ alkylenearyl, or
7) $C_0$–$C_{10}$ alkylene-$NR^5R^6$;

$R^5$ and $R^6$ are independently:
1) H,
2) ($C_1$–$C_8$ alkyl)—$(R^7)_2$,
3) (C=O)O($C_1$–$C_8$ alkyl),
4) 9-fluorenylmethylcarbonyl,
5) $OCH_2OCH_2CH_2Si(CH_3)_3$,
6) (C=O)($C_1$–$C_8$ alkyl),
7) (C=O)$CF_3$, or
8) ($C_2$–$C_8$ alkenyl)—$(R^7)_2$, or $R^5$ and $R^6$ are taken together with the nitrogen to which they are attached to form N-phthalimido;

$R^7$ is:
1) H,
2) OH,
3) $OC_1$–$C_6$ alkyl, or
4) aryl, said aryl optionally substituted with up to two groups selected from OH, O($C_1$–$C_6$ alkyl), and ($C_1$–$C_3$ alkylene)—OH;

which comprises the steps of:
(a) reacting a furanose or a pyranose with an activating reagent to produce an activated sugar; and
(b) coupling the activated sugar with a compound of Formula IV

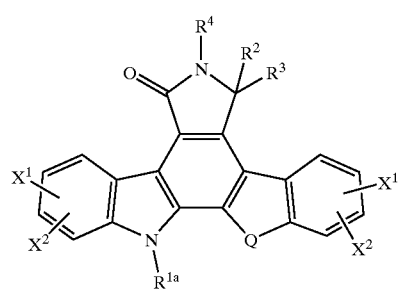

IV wherein $R^{1a}$ is H if Q is O, S, $CH_2$, or N—R and R is not H, otherwise $R^{1a}$ is selected from $R^1$;

in the presence of an aqueous solution of alkali hydroxide and a phase transfer catalyst in a biphasic system to produce the compound of Formula I.

2. The process of claim 1, wherein

R and $R^1$ are independently selected from a furanose group of Formula IIA or a pyranose group of Formula IIB, when R or $R^1$ is defined as a furanose group or a pyranose group, respectively;

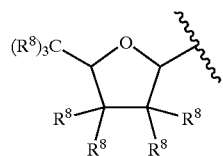

IIA

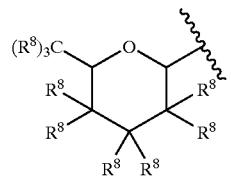

IIB $R^8$ is independently selected from:
1) hydrogen,
2) $C_1$–$C_6$ alkyl,
3) OH,
4) halogen,
5) O($C_1$–$C_6$ alkyl),
6) O($C_1$–$C_6$ alkylene)-aryl,
7) $OSO_2$($C_1$–$C_6$ alkyl),
8) $OSO_2$aryl,
9) $OCH_2OCH_2CH_2Si(CH_3)_3$,
10) O(C=O)($C_1$–$C_6$ alkyl),
11) O(C=O)$CF_3$,
12) azido, or
13) $NR^5R^6$, or
two $R^8$'s on the same carbon are taken together to be oxo, =N—$R^5$, or =N—$R^7$; and the furanose or pyranose in Step (a) is a furanose of Formula IIIA or a pyranose of Formula IIIB, respectively;

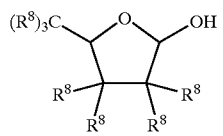

IIIA

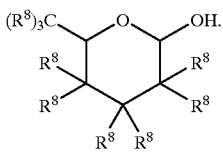

IIIB

3. The process according to claim 2 wherein the activating reagent in Step (a) is selected from an acid halide and the biphasic system in Step (b) is comprised of an organic solvent selected from a hydrocarbon, a nitrile, an ether, a halogenated hydrocarbon, a ketone, or an apolar aprotic solvent.

4. The process according to claim 3 wherein the activating reagent is selected from $SOCl_2$ or oxalyl chloride.

5. The process according to claim 3 wherein the biphasic system is comprised of methyl-t-butyl ether, dichloromethane, or trifluorotoluene.

6. The process according to claim 3 wherein the phase transfer catalyst in Step (b) is $(R^a)_4M+A-$;

$R^a$ is independently H or $C_1$–$C_{18}$ aliphatic hydrocarbon;
M is N or P; and
A is OH, F, Br, Cl, I, $HSO_4$, CN, $MeSO_3$, or $PhCH_2CO_2$.

7. The process according to claim 6, wherein the phase transfer catalyst is tricaprylmethyl ammonium chloride.

8. The process according to claim 3, wherein the aqueous solution of alkali hydroxide in Step (b) has a concentration of about 5% to about 95% w/w and the alkali hydroxide is selected from lithium hydroxide, sodium hydroxide, potassium hydroxide, and cesium hydroxide.

9. The process of claim 8 wherein the aqueous solution of alkali hydroxide has a concentration of about 45% to about 50% w/w and the alkali hydroxide is potassium hydroxide or sodium hydroxide.

10. A process for the preparation of a compound of Formula V,

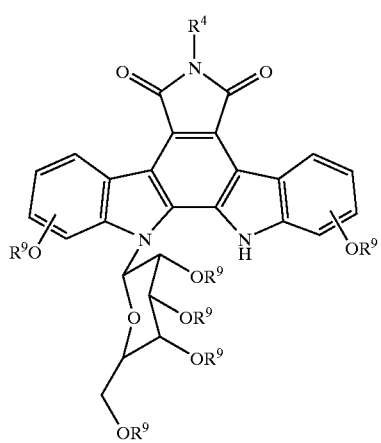

V wherein
$R^4$ is:
1) H,
2) $C_1$–$C_{10}$ alkyl,
3) CHO
4) (C=O)$C_1$–$C_{10}$ alkyl,
5) (C=O)O$C_1$–$C_{10}$ alkyl,
6) $C_0$–$C_{10}$ alkylenearyl, or
7) $C_0$–$C_{10}$ alkylene-$NR^5R^6$;
$R^5$ and $R^6$ are independently:
1) H,
2) ($C_1$–$C_8$ alkyl)—($R^7)_2$,
3) (C=O)O($C_1$–$C_8$ alkyl),
4) 9-fluorenylmethylcarbonyl,
5) OCH$_2$OCH$_2$CH$_2$Si(CH$_3$)$_3$,
6) (C=O)($C_1$–$C_8$ alkyl),
7) (C=O)CF$_3$, or
8) ($C_2$–$C_8$ alkenyl)—($R^7)_2$, or
$R^5$ and $R^6$ are taken together with the nitrogen to which they are attached to form N-phthalimido;
$R^7$ is:
1) H,
2) OH,
3) O$C_1$–$C_6$ alkyl, or
4) aryl, said aryl optionally substituted with up to two groups selected from OH, O($C_1$–$C_6$ alkyl), and ($C_1$–$C_3$ alkylene)—OH;
$R^9$ is:
1) H,
2) $C_1$–$C_6$ alkyl,
3) ($C_1$–$C_6$ alkylene)-aryl,
4) SO$_2$($C_1$–$C_6$ alkyl),
5) SO$_2$aryl,
6) CH$_2$OCH$_2$CH$_2$Si(CH$_3$)$_3$,
7) (C=O)($C_1$–$C_6$ alkyl), or
8) (C=O)CF$_3$;
which comprises the steps of:
(a) reacting a sugar derivative of Formula VI with an acid chloride to produce the activated sugar; and

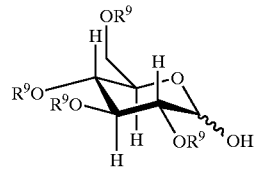

VI (b) coupling the activated sugar with a compound of Formula VII

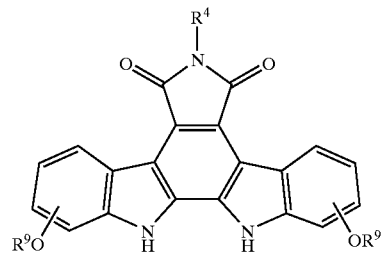

VII in the presence of an aqueous solution of an alkali hydroxide and tricaprylmethyl ammonium chloride in t-butyl methyl ether to produce the compound of Formula V.

11. A process for the preparation of a compound of Formula VIII,

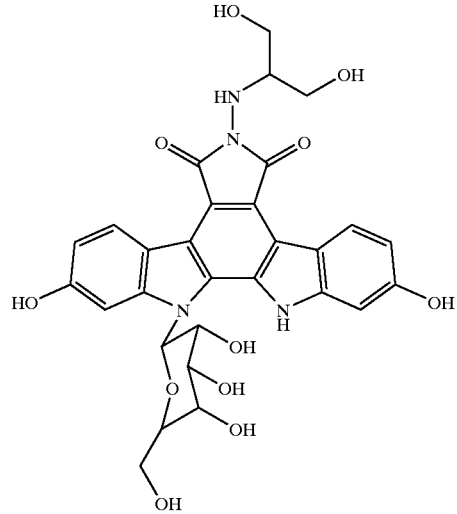

VIII which comprises the steps of;

(a) reacting a sugar derivative of Formula IX with thionyl chloride to produce the activated sugar;

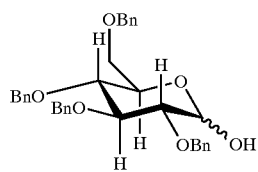

IX (b) coupling the activated sugar with a compound of Formula X

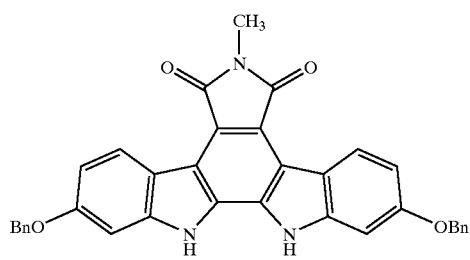

X in the presence of an aqueous solution of potassium hydroxide or sodium hydroxide and tricaprylmethyl ammonium chloride in t-butyl methyl ether to form the glycosidated compound XI;

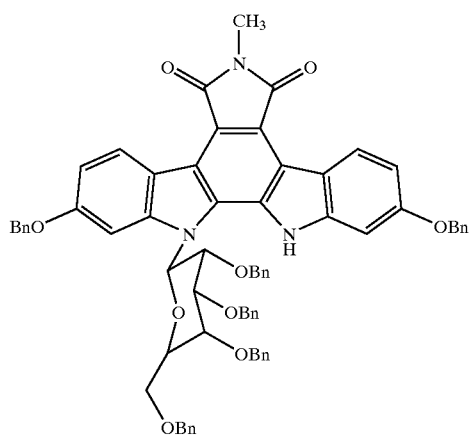

XI (c) deprotecting the glycosidated product XI by reacting it with catalytic palladium in the presence of hydrogen gas to form the deprotected glycosidated product XII;

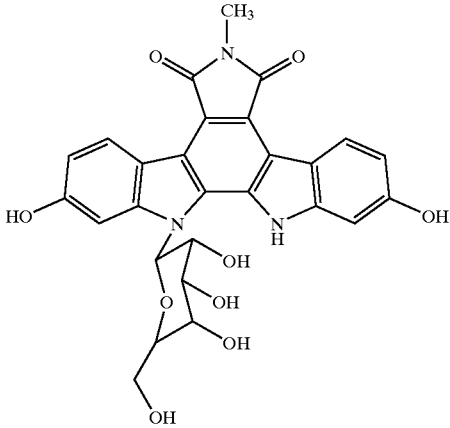

XII (d) reacting the deprotected glycosidated product XII with an aqueous solution of alkali hydroxide to form anhydride XIII; and

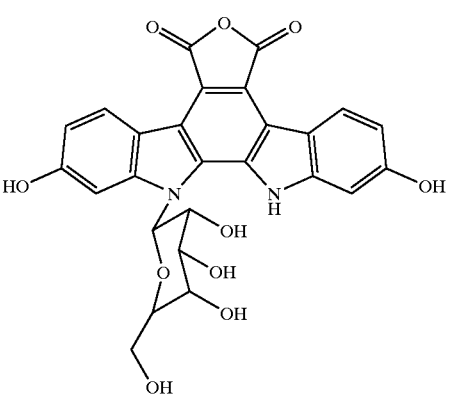

XIII (e) reacting anhydride XIII with 2-hydrazino-1,3-propanediol to produce the compound of Formula VIII.

12. The process of claim 10 wherein Step (A) is conducted in t-butyl methyl ether or tetrahydrofuran at a temperature of about −10° C. to about 30° C. and Step (B) is conducted at a temperature of about 0° C. to about 40° C.

13. The process of claim 12, wherein the potassium hydroxide or sodium hydroxide in step (b) is added before the tricaprylmethyl ammonium chloride.

* * * * *